United States Patent
Schwaibold et al.

(10) Patent No.: US 9,801,589 B2
(45) Date of Patent: Oct. 31, 2017

(54) DEVICE AND METHOD FOR DETERMINING A COMPARISON VALUE OF BIODATA AND FOR RECORDING BIODATA

(75) Inventors: Matthias Schwaibold, Karlsruhe (DE); Dirk Sommermeyer, Karlsruhe (DE); Bernd Schöller, Karlsruhe (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 2078 days.

(21) Appl. No.: 12/225,980

(22) PCT Filed: Apr. 4, 2007

(86) PCT No.: PCT/DE2007/000614
§ 371 (c)(1),
(2), (4) Date: Jun. 1, 2009

(87) PCT Pub. No.: WO2007/115553
PCT Pub. Date: Oct. 18, 2007

(65) Prior Publication Data
US 2009/0240119 A1    Sep. 24, 2009

(30) Foreign Application Priority Data

Apr. 7, 2006  (DE) .................. 10 2006 018 040
Apr. 7, 2006  (DE) .................. 10 2006 018 041

(51) Int. Cl.
*A61B 5/00* (2006.01)
*A61B 5/024* (2006.01)

(52) U.S. Cl.
CPC .............. *A61B 5/7275* (2013.01); *A61B 5/00* (2013.01); *A61B 5/0006* (2013.01); *A61B 5/02405* (2013.01); *A61B 5/02416* (2013.01); *A61B 5/02438* (2013.01)

(58) Field of Classification Search
CPC ................................ A61B 5/7275; A61B 5/00
USPC ................................ 600/513, 508, 509, 300
See application file for complete search history.

(56) References Cited

U.S. PATENT DOCUMENTS 6,216,032 B1 *  4/2001  Griffin et al. ................. 600/515
6,340,346 B1 *  1/2002  Almog et al. ................. 600/300

FOREIGN PATENT DOCUMENTS

EP    1440653 A1 *  7/2004  ............... A61B 5/00

* cited by examiner

*Primary Examiner* — Nadia A Mahmood
(74) *Attorney, Agent, or Firm* — Abel Law Group, LLP

(57) ABSTRACT

The method and the device are used for evaluating recorded measurement data. In particular, the use of the method and of the device makes it possible to detect the individual risk of a living being in respect of certain disease states and, if appropriate, to automatically evaluate correspondingly recognized risks in a device control. Measurement data in respect of heart-specific and/or circulation-specific parameters or respiration-specific parameters of a patient are preferably recorded and evaluated. The measurement data are determined over a defined period of time and the measurement data are evaluated taking into account the time information. A particularly effective implementation of the method can be based on pattern recognition in which individual patterns and/or sequence patterns are evaluated.

30 Claims, 10 Drawing Sheets

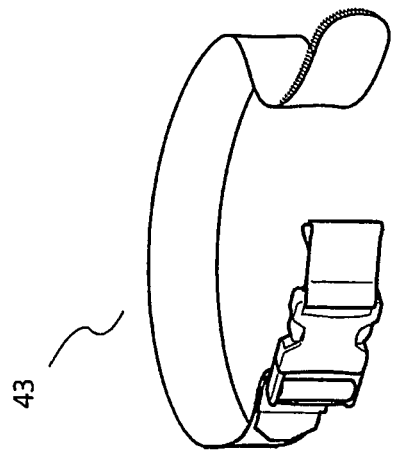
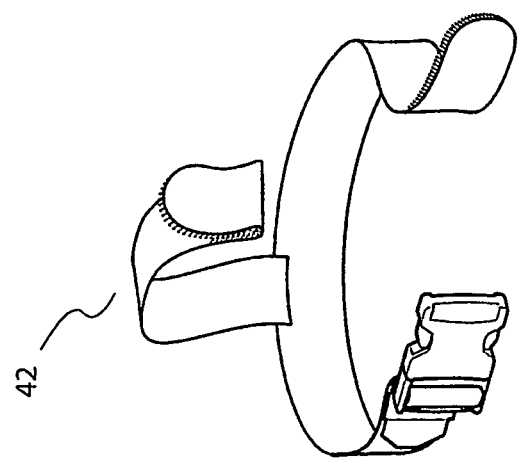
Fig. 4

DEVICE AND METHOD FOR DETERMINING A COMPARISON VALUE OF BIODATA AND FOR RECORDING BIODATA

The device and the method pertain to a system for determining a reference value of biophysical data (body parameters) of an individual for determining individual risk, which system consists of at least one sensor for the noninvasive measurement of at least two signals, which are selected from the following group: CWF (continuous wave fluctuation), SpO2, heart rate, and PTT (pulse transit time), and an evaluation unit connected to the sensor, wherein the evaluation unit has at least one analyzer, which determines signal ranges that can be defined by signal analysis.

Preferably, a plethysmogram is used, which is recorded, for example, with a pulse oximeter. Various CWP's (continuous wave parameters) are extracted from the plethysmogram. CWP's are various fluctuating parameters that each describe a characteristic of the plethysmogram. For example, the following quantities can be computed as CWP's: the pulse wave amplitude, the integral over certain intervals of the plethysmogram, the ratio of different integrals over different intervals of the plethysmogram, a portion of the plethysmogram that is correlated with respiration, the angle of rise of each pulse wave, the angle of fall of each pulse wave, the ratio of the angle of rise to the angle of fall, the duration of a pulse wave rise, the duration of a pulse wave fall, the ratio of the duration of rise to the duration of fall, the pulse wave maximum, the pulse wave minimum, and a quantity related to the PTT (pulse transit time). In accordance with the invention, any parameter that describes a characteristic of a segment of the plethysmogram may be represented as a CWP.

If CWP's are considered as a function of time, a CWF (continuous wave fluctuation) signal can be computed from it, which is subject to fluctuations that are relevant for the signal analysis. The CWF signal thus contains information about the fluctuations of the plethysmogram or of the CWP's derived from it. It is possible to represent one of the following quantities as a CWF signal: the pulse wave amplitudes, parameters related to the integral over an interval of the plethysmogram, ratios of different integrals over different intervals of the plethysmogram, portions of the plethysmogram that are correlated with respiration, angles of rise of the pulse waves, angles of fall of the pulse waves, ratios of angles of rise to angles of fall, durations of pulse wave rises, durations of pulse wave falls, ratios of the durations of rises to the durations of falls, the envelope of the pulse wave maxima or pulse wave minima, quantities related to the PTT (pulse transit time), the median line of the plethysmogram, and the pulse rate. However, it is also possible to use the PTT or other signals that are subject to fluctuations to determine a CWF. In accordance with the invention, any fluctuation of the plethysmogram, every CWP and every combination of different CWP's may be represented as CWF signals.

A problem that exists is that of determining a risk index, which assists with the diagnosis, stabilization, and monitoring of individuals and can be determined by hospital tests and ambulatory tests.

In many diseases, there are dependent relationships on or interactions with cardiovascular diseases, which can affect the quality of life of the patient. In the past, it has been possible to determine these kinds of phenomena only statistically for a group of patients and not for a specific patient.

Various measuring methods for determining individual parameters related to the autonomic regulation of the cardiovascular system are already known. Measuring methods of this type are described, for example, in U.S. Pat. No. 5,862,805, WO 91/11956, US 2002-0029000, WO 02/067776, and EP 0 995 592. However, so far no methods and devices have been disclosed which relate to a comprehensive evaluation of individual measured values for the comprehensive consideration of individual factors in the determination of an individual risk index.

In particular, no device presently exists which makes it possible, on the basis of the parameters it measures, to make predictions about the individual risk that the patient's present disease, which is possibly but not necessarily diagnosed with the same device, might lead to the development of secondary diseases that adversely affect quality of life or life expectancy.

Similarly, no device presently exists which makes it possible, on the basis of combinations of the parameters it measures, to provide information about whether existing therapeutic measures and therapeutic dosages for the disease, which is possibly but not necessarily diagnosed with the same device, are qualitatively and/or quantitatively suitable.

The device and method of the invention also concern a modular system for determining biophysical data of an individual, which consists of at least one sensor device for the noninvasive measurement of at least two signals.

This is intended for determining, for example, sleep-related disorders and/or cardiovascular diseases and/or metabolic diseases, and for aiding in the making of a diagnosis. At present, a determination of sleep-related disturbances or disorders is always made by a specialized physician and usually overnight in a sleep laboratory. A polysomnograph is usually used for this purpose. Due to the small number of specialized physicians trained in this discipline and the small number of sleep laboratories, many patients often have to wait long periods of time, before a diagnosis can be made, if indeed a diagnosis is ever made.

Therefore, one of the objectives of the invention is to make available a device that allows a diagnosis to be made quickly, easily and inexpensively. In addition, expanded information, compared to the previously used polysomnography, is to be made available by evaluating parameters of the pulse wave. This expanded information should relate especially to the activity and evaluation of the autonomic nervous system.

In particular, there are no devices at all with fewer input channels than polysomnographs which allow the establishment of a diagnosis that is comparable to that of a polysomnograph or is superior with respect to specific questions.

Therefore, another objective of the invention is to design a device and a method of the aforementioned type in such a way that individual applicability to a patient can be realized.

In accordance with the invention, these objectives are achieved by the features of claim 1 and by the steps of the method specified in claim 5.

In this connection, at least one sensor for the noninvasive measurement of at least two signals, which are selected from the following group: CWF (continuous wave fluctuation), SpO2, heart rate, and PTT (pulse transit time), is connected to an evaluation unit, the evaluation unit has at least one analyzer, the analyzer determines signal ranges that can be defined by signal analysis, a comparator analyzes the signal ranges, taking additional parameters into account, and the result of the analysis is transmitted as an index value to a connected output device.

The goal of the invention is thus neither the diagnosis of a disease nor the pure determination of the frequency and severity of the occurrence of certain pathophysiological events. The goal rather is to use the detected signals to determine the tested person's individual level of risk for suffering secondary diseases that adversely affect quality of life or life expectancy. Likewise, the form of therapy and the therapeutic dosage that are optimum for the person can be derived from the determined risk. In addition, the success of a therapy that is already in use can be measured.

By evaluating at least two signals selected from the following group: CWF (continuous wave fluctuation), SpO2, heart rate, and PTT (pulse transit time), for example, by the use of photoplethysmography, it is possible to determine the interactions of a plurality of physiological and pathophysiological processes. In addition, it is possible that with the use of a significantly reduced number of measuring sensors compared to the prior art, namely, only one measuring sensor, for example, in the form of a pulse oximetry sensor, information can be obtained that is comparable to that provided by prior-art methods, for example, in regard to respiratory disorders, sleep disorders, diabetes, inflammatory reactions, vascular conditions and cardiovascular diseases.

It is thus possible to obtain individual information about a patient's state of heath with respect to:
cardiovascular risk
stress
diabetes
inflammatory states
autonomic functional disturbances and diseases related to them
risk index (percent)
class risk groups
differentiation of the risk factors/treatment necessary yes/no A further objective of the invention is to provide a modular device that makes it possible to quickly and easily adapt modules that can be supplemented as needed.

Likewise, there are no devices at all that can be adapted according to need, but rather the polysomnographs that are presently in use are equipped with all channels, even when only a few channels would be sufficient and useful for the current investigation.

Therefore, another objective of the present invention is to design a device of the aforementioned type in such a way that it is possible to realize individual applicability to a patient in the sense that for an individual patient, only the specific modules that are actually necessary are used for the analysis. To carry out more extensive analyses, additional modules can be quickly and easily adapted to the basic module. A special advantage of the device of the invention is that even medical laymen but certainly at least medical personnel or physicians with no special training in this field are immediately able to apply the device of the invention to the patient quickly and correctly.

In accordance with the invention, this objective is achieved by virtue of the fact that a basic module has interfaces for adapting individual supplementary modules for determining additional biophysical data, such as EKG, heart rate, respiratory flow, and PTT (pulse transit time).

A plethysmogram is preferably recorded, for example, with a pulse oximeter and/or a multiple wavelength pulse spectrometer (according to DE 10 2005 020022 A1, DE 102 13 692 A1 and DE 103 21 338 A1). The terms pulse oximeter and pulse spectrometer are used synonymously here. The pulse oximeter and/or pulse spectrometer use at least two wavelengths selected from the range of 400 to 2500 nm to determine at least the following parameters: pulse rate, plethysmogram and oxygen saturation (SpO2 and/or SaO2). Therefore, in the discussion which follows, the terms SpO2 and SaO2 are used synonymously.

At least one CWP (continuous wave parameter) and preferably at least two CWP's are extracted from the plethysmogram.

In accordance with the invention, different signals can be combined to detect relevant fluctuations in the pulse wave and to use them for the evaluation.

For example, it is possible to undertake a differentiation of obstructive and central respiratory disorders on the basis of patterns detected in a CWF signal derived from the plethysmogram. In this regard, the characteristic patterns have frequency components that are related to the respiratory rate.

Signal analysis over a predeterminable period of time is assisted if the sensor is connected to a first memory unit for storing a detected test signal.

To carry out pattern analysis of the detected signal, it is proposed that the evaluation unit have a pattern analyzer for analyzing the behavior of the signal with respect to time.

To further improve the evaluation possibilities, it is proposed that the comparator be provided with a second memory unit for storing the calculated index value.

A typical evaluation sequence is carried out by evaluating the amplitude behavior of the test signal.

It is also contemplated that the slope of the test signal be evaluated.

In accordance with another embodiment of the invention, it is proposed that the frequency of the test signal be evaluated.

With respect to the predictive sensitivity, it has been found to be especially advantageous for the intensity of change of the test signal to be evaluated.

Comprehensive signal analysis can be accomplished by carrying out pattern recognition.

Additional signal analysis can be accomplished by carrying out periodic and/or transient signal analysis.

Supplementary signal analysis can be accomplished by carrying out a frequency analysis.

An alternative signal analysis can be accomplished by carrying out an analysis of the slope.

A signal analysis can be accomplished by forming histograms and/or distributions and/or derivatives.

An alternative signal analysis can be accomplished by comparing and/or correlating threshold values.

Signal analysis can be further assisted by plotting a hierarchy of signals and/or a decision tree.

One possibility for signal acquisition consists in the evaluation of a CWF (continuous wave fluctuation) signal.

For example, the amplitudes 51 of the plethysmogram 49 are used to determine a CWF signal. In this case, the CWF 50 represents the amplitude levels of the individual pulse waves of the plethysmogram 49.

However, it is also possible to use the PTT or other signals that are subject to fluctuations to determine a CWF.

In accordance with the invention, different signals can be combined to detect relevant fluctuations of the pulse wave and to use for the evaluation.

Another possibility for signal acquisition consists in the evaluation of an oxygen saturation signal.

Another possibility for signal acquisition consists in the evaluation of a pulse rate or heart rate signal.

Another possibility for signal acquisition consists in evaluation of a PTT (pulse transit time).

A supplementary possibility for signal acquisition consists in the evaluation of an EEG signal.

It is likewise contemplated that an EKG signal be evaluated.

It is likewise contemplated that an EMG signal be evaluated.

Another measurement variant consists in the evaluation of the oxygen saturation of the blood.

Another measurement variant consists in the evaluation of the hemoglobin concentration of the blood.

To determine respiratory parameters, it is proposed that a respiratory pattern be evaluated.

To determine other parameters, it is proposed that supplementary evaluations of the following can be performed: snoring, arousal, blood pressure, CO2, sleep stages, skin conductance, depth of sleep, sleep fragmentation, activity of the parasympathetic nervous system, absolutely or in relation to the sympathetic nervous system, and vascular compliance.

A measurement principle that is simple to realize consists in the evaluation of optical density of at least one body region.

In accordance with a typical evaluation method, it is provided that a signal analysis is carried out with respect to presently existing periodic signal components.

An evaluation of especially predictive signal patterns is realized by carrying out an analysis with respect to a maximum signal change.

In particular, it has been found to be advantageous to assign the index of a cumulative autonomic resting intensity to the regulation of the cardiovascular system.

The detection of especially predictive events is accomplished by carrying out a signal analysis with respect to a period of activation of the autonomic nervous system A further increase in the quality of prediction can be achieved if, in the evaluation of periods of activation of the autonomic nervous system, at least one other parameter is evaluated. The increase in the quality of prediction can be achieved by comparing the change of various detected parameters or parameters derived from the detected parameters at the time of an activation of the autonomic nervous system in intensity, type and sequence with respect to time.

To eliminate disturbances or singular events, it is proposed that in the determination of the index, the cumulative number and the intensity of activation periods of the autonomic nervous system be taken into consideration.

It is conducive to a simple measurement setup if the sensor determines the heart rate.

In particular, it is contemplated that the sensor determines the variability of the heart rate.

It is also possible for the sensor to determine the PTT.

It is also possible for the sensor to determine a CWF.

Alternatively, it is possible for the sensor to determine the pulse amplitude.

To suppress problems, it is helpful to carry out artifact detection and elimination before the evaluation of the determined parameters.

Detection of short-term signal changes is assisted by evaluating a maximum value of the test signal detected by the sensor that appears within a predetermined interval of time.

A measuring method that is simple to apply consists in carrying out the signal acquisition with the use of photoplethysmography.

An increase in the sensitivity of the system can be realized by carrying out the signal analysis within at least one predeterminable frequency band.

To take interactions into consideration, it is proposed that at least one other body parameter is evaluation by the evaluation unit.

For example, it is possible to evaluate the age of the individual as an additional body parameter.

It is also possible to evaluate the sex of the individual as an additional body parameter.

Alternatively or additionally, it is also possible to evaluate the weight of the individual as an additional body parameter.

Alternatively or additionally, it is also possible to evaluate one or more risk factors that are already known, for example, risk factors for cardiovascular disease, as additional body parameters.

Alternatively or additionally, it is also possible to evaluate one or more factors that are already known which affect the autonomic regulation, especially medication, as additional body parameters.

Alternatively or additionally, it is also possible to evaluate one or more additionally determined parameters, e.g., arterial oxygen saturation, as additional body parameters.

Past events can be taken into consideration by evaluating the medical history of the individual as an additional body parameter.

A further increase in the quality of prediction can be realized by evaluating the medication of the individual.

A further increase in the quality of prediction can be realized by evaluating reference values of other persons as additional parameters.

In accordance with the invention, at least the following signals are determined, for example, with a pulse oximeter sensor: continuous wave fluctuation: CWF, SpO2, pulse rate.

In addition, suitable sensors can be added to record and analyze respiratory signals, such as flow, pressure or snoring, heart rate, and PTT (pulse transit time). The use of EKG signals, EEG signals and EMG signals for the evaluation is likewise contemplated. In addition, blood pressure and CO2 concentration can be recorded and used for the evaluation.

At least one of the following methods is used to evaluate the signals:

pattern recognition
    signal analysis (harmonic/transient)
    frequency analysis
    slope analysis
    histograms, distributions, derivatives, integrations
    combination of (statistically) different factors, measured values, determined values
    event data, long-term trend
    threshold value comparison
    correlation
    hierarchy of signals
    decision tree
    digital filtering
    wavelet analysis
    temporary storage of signal segments, CWP segments or CWF segments
    entropy, standard deviation
    methods of chaos theory The result produced by the device of the invention is a risk index specific to the patient. This index can be expressed, for example, as a percentage. For this purpose, the medical history of the patient is preferably considered along with the current measurement data for the determination of the risk index. At least on read-out memory in the vicinity of the device is used as a data base.

In addition, the following output options are alternatively and/or additionally provided in accordance with the invention:
- indication of the cardiovascular risk/stress
- indication of the risk of developing diabetes
- indication of the risk of developing inflammatory conditions
- indication of autonomic functional disturbances and diseases related to them
- indication of classes and/or risk groups In accordance with the invention, a differentiation of the risk classes is also provided. On the basis of the output of the device of the invention, it is possible, for example, for a physician to initiate targeted treatment.

In accordance with a preferred variant of the invention, first the CWP is computed from at least one test signal. The CWF is then optionally determined from the original test signal, the CWP, or both the test signal and the CWP.

The determined CWF can be used, for example, as part of an automated diagnostic system. However, besides that, it is also possible to evaluate the CWF directly for a device control.

In order to carry out more extensive analysis, the CWF can be compared with stored values or patterns or with current measured values.

The invention is explained below with reference to practical examples.

FIG. 4 shows belts for attaching the device.

Figure 1:
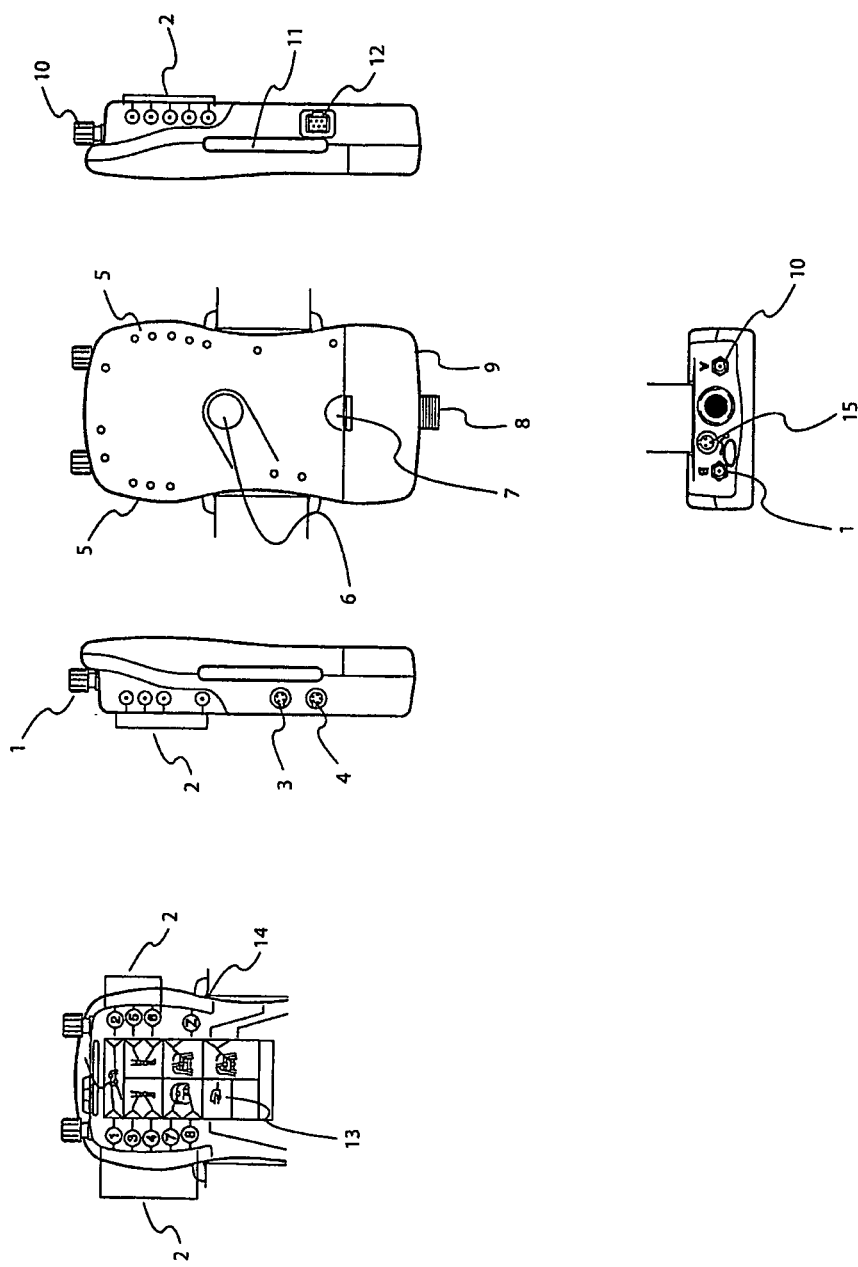
FIG. 1 shows several views of a device for determining values.

In a preferred embodiment of the invention, the device makes it possible to make a fast determination of the risk index by using a pulse oximetry sensor to make essentially simultaneous determinations of at least three signals, namely, CWF, oxygen saturation of the blood, and pulse rate. The signals are analyzed by pattern recognition and compared with stored values. In particular, the change of the amplitude of the pulse wave is analyzed. The result of the comparison yields a patient-specific risk index that is suitable for predicting the risk of a cardiovascular disease. The device of the invention is small and portable. Power is supplied alternatively by batteries/rechargeable batteries and/or a power cable.

The measured data are stored in the device on a CompactFlash® card and transmitted to the PC online via cable or, optionally, wirelessly. For ambulatory use, the data stored in the device can either be transmitted to the PC via a USB interface or read into the software by reading out the CompactFlash® card via a reader.

The device of the invention for determining and analyzing biophysical data of an individual consists of a basic module with a power supply, a memory unit and at least one sensor device for the noninvasive measurement of at least one test signal that represents cardiac activity and/or respiratory activity. The sensor device can be selected, for example, from the following group: EKG, sphygmomanometer cuff, pulse oximeter, impedance sensor, and Doppler sensor.

The test signal that represents the cardiac activity and/or the respiratory activity is selected from the following group: pulse rate, plethysmogram, oxygen saturation, respiratory signal, and heart signal. The sensor device is connected to an analyzer for extracting at least one CWP (continuous wave parameter) from the test signal and/or a device for determining at least one CWF (continuous wave fluctuation), such that the CWF (continuous wave fluctuation) is preferably determined from the CWP and/or the test signal.

A classifier compares at least one CWF datum and/or quantities derived from it with stored data in order to identify physiological/pathophysiological events from this information. The events in question include, for example, apnea, with it being possible, in accordance with the invention, to distinguish between central and obstructive apneas.

In another embodiment, a classifier compares at least one CWF datum and/or quantities derived from it with other test signals and/or CWP's in order to identify physiological/pathophysiological events from this information.

At least some of the results of the analyzer and/or at least some of the results of the classifier are output basically immediately, acoustically and/or graphically, preferably via a display.

In accordance with the invention, to identify physiological events, at least two signals that are temporally related are evaluated.

The device of the invention can be expanded with supplementary modules for measuring other signals. To this end, the modules are preferably adapted as "plug and play" modules. Supplementary sensor devices are preferably adapted for this purpose.

To this end, at least one interface is installed in the basic module and/or in supplementary modules.

The interface also allows data to be read out and/or other devices, especially therapeutic devices, to be controlled.

At least the following alternative or supplementary adaptable sensor devices are provided: EKG, EMG, EOG, EEG, pulse oximetry, blood pressure, impedance measurement, ultrasound, Doppler, CO2, respiratory flow, snoring, mouth, thorax, abdomen, position sensors.

The sensor devices can be supplemented in the form of a module that is designed, for example, to determine respiratory parameters, such as respiratory flow, PTT, movement signals, and respiratory effort.

The sensor devices can also be supplemented in the form of a module that is designed, for example, to determine cardiological parameters, such as EKG and heart rate.

A data input device is provided for inputting patient data, for example, age, sex and state of health.

A display is provided as a means of displaying analytical results. Acoustic alarms are also provided.

In accordance with the invention, at least the basic module is detachably mounted on the body of a patient with fastening means, such as belts.

In another embodiment, the device for determining and analyzing biophysical data of an individual consists of at least one sensor device for the noninvasive measurement of at least two signals, such as a plethysmogram and CWF (continuous wave fluctuation) signals derived from it, SpO2 and pulse rate, and an analyzer connected to the sensor device for analyzing transient and/or periodically recurring patterns of the measured signals. This is supplemented by a module for the evaluation of information that is related to the frequency or amplitude of the signals or the parameters derived from them.

In a supplementary embodiment, the device for determining and analyzing biophysical data of an individual consists of a basic module with a power supply, a memory unit and at least one sensor device for the noninvasive measurement of at least one test signal that represents the respiratory activity, for example, oxygen saturation, respiratory signal or flow signal, and at least one additional sensor device for the noninvasive measurement of at least one test signal that represents the cardiac activity, for example, oxygen saturation, blood pressure, pulse rate, EKG or plethysmogram, and an analyzer connected to the sensor device for extracting at least one CWP (continuous wave parameter) from at least one of the test signals.

For example, conclusions can be drawn about apneas, hypopneas and other respiratory disturbances. By using at least one sensor device for the noninvasive measurement of at least one test signal that represents the respiratory activity and at least one other sensor device for the noninvasive measurement of at least one test signal that represents the cardiac activity, it is possible to draw conclusions about diseases of the cardiovascular system and/or the respiratory system, for example, by pattern analysis.

Additional embodiments are described below.
Application portion, consisting of:
- basic module
- cardiology module
- pneumology module
- application parts
- battery/rechargeable battery, e.g., lithium ion battery
- medically acceptable power supply unit (secondary side) with all-purpose cable for charging the rechargeable battery and for transmitting the stored data to a PC via a galvanically separated USB interface (converter box)

PC Software:
The software can be operated under the operating systems Windows 2000, SP 2 and higher, Windows XP Professional and Home Edition.

Nonmedical electrical devices:
- power supply unit (primary side)
- USB-TCP/IP converter
- Bluetooth®-USB adapter
- CompactFlash® card reader
- PC system (external accessories)

Figure 9:
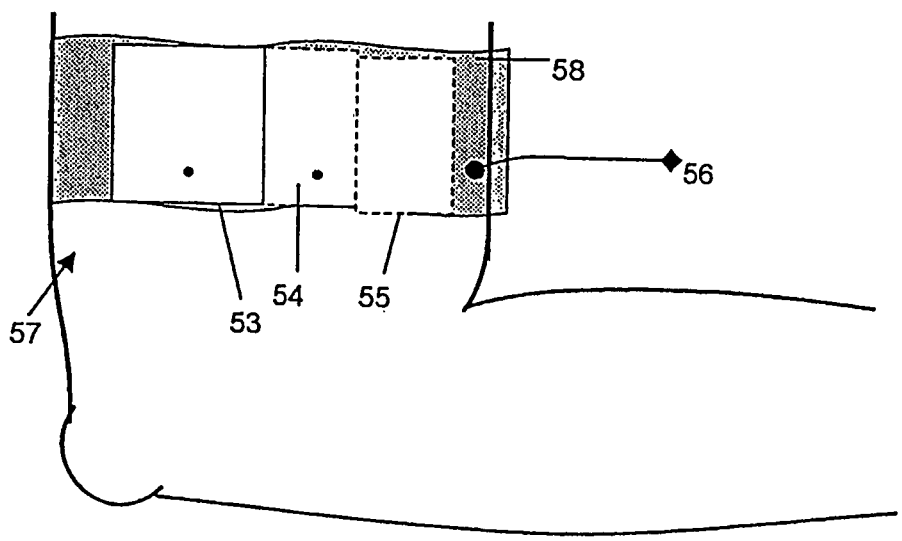
FIG. 9 shows an arm cuff with a basic module and two supplementary modules mounted on it.
Figure 10:
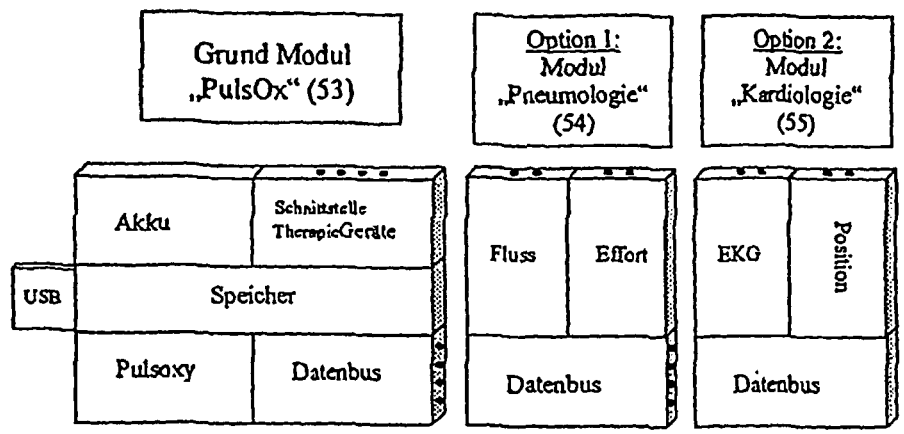
FIG. 10 shows a basic diagram with a basic module and two supplementary modules assigned to it.

Basic Module
The basic module consists of a pulse oximeter, a possible interface for controlling other devices, e.g., therapeutic devices, possible additional interfaces for additional, optional sensors, e.g., connection of a respiratory flow/snoring sensor, a communications interface, for example, USB, or a wireless protocol, a readable memory, a power supply via battery/rechargeable battery and a data bus controller as a connection for additional modules, and a display for displaying computed indices, current measured values and current battery/rechargeable battery states. For relaying the determined data, the basic module allows bidirectional data exchange with other devices, for example, with APAP machines. FIG. 9 shows how the basic module 53, an adapted pneumology module 54 and an adapted cardiology module 55 are positioned on a common carrier 58 on the arm 57 of a user. Bidirectional data transmission is possible via the connected cable 56. Alternative application sites for the device of the invention are: the finger, toe, nose, ear, and forehead.

The device of the invention has fewer input channels than standard polysomnographs and is thus considerably less expensive, smaller, lighter and more energy-efficient.

Sensors:
Pulse oximetry sensor for recording a plethysmogram and determining oxygen saturation and pulse rate.

The basic module can determine the following values:
- pulse rate
- oxygen saturation (SpO2)
- RDI and AHI (in each case differentiated as obstructive or central)
- risk value for obstructive respiratory tract disease
- risk value for central respiratory disturbance
- risk value for PLM (periodic leg movement)
- characteristic value for the recovery function of sleep
- autonomic (micro) arousal index
- sleep quality index
- index for respiratory events
- autonomic status
- characteristic value for current concentration ability
- characteristic value for high tiredness
- characteristic value for high sleep pressure
- autonomic rest
- index for cardiovascular risk (vascular disease, rhythmological disease, cardiac insufficiency)
- leakage, therapeutic success
- index for the progression of a disease Pneumology Module
This module can be adapted to the data bus of the basic module to carry out additional analyses. In accordance with the invention, it is possible to realize the connection between the basic module and the pneumology module as a plug connection, which can be handled quickly and easily. The pneumology module can also be used by itself, without the basic module. The pneumology module has at least one effort sensor system and one sensor device for determining a respiratory flow signal.

Possible Sensors
effort sensors:
(thoracic and abdominal movements);
respiratory flow/snoring sensor (thermistors and microphone);
respiratory flow/snoring eyeglasses (pressure sensor);
oral thermistor for determining mouth breathing in therapeutic monitoring;
pneumo-T-adapter for determining respiratory flow, snoring, and xPAP pressure (differential pressure sensor).

In conjunction with the basis module, the pneumology module can determine the following values:
- RDI/AHI (apnea/hypopnea differentiation)
- arousals that are related to a respiratory event
- differentiation of RERAs and arousals that are related to apnea/hypopnea events
- differentiation of obstructive and central events
- flattening
- snoring
- upper airway resistance syndrome
- respiratory effort, work of breathing Cardiology Module
The cardiology module makes it possible to record an EKG. A position sensor can be adapted to supplement it. This module can be adapted to the data bus of the basic module for carrying out additional analyses. In accordance with the invention, it is proposed that the connection between the basic module and/or pneumology module and cardiology module be realized as a plug connection, which can be handled quickly and easily. The cardiology module can also be used alone, without the basic module and/or pneumology module.

The cardiology module can determine the following values:
EKG
heart rate variability
pulse transit time (PTT)
position-dependent events In accordance with the invention, it is proposed that other modules be adapted as needed.

Individual device components are described in detail below.
electrodes for the electrophysiological channels;
effort sensors (thoracic and abdominal movements);
pulse oximetry sensor for determining oxygen saturation, pulse rate, pulse wave, CWF and PTT;
respiratory flow/snoring sensor (thermistors and microphone);
respiratory flow/snoring eyeglasses (pressure sensor);
oral thermistor for determining mouth breathing in therapeutic monitoring;
pneumo-T-adapter for determining respiratory flow, snoring and xPAP pressure (pressure sensor).

Converter Box and Power Supply Unit

The converter box is used for cable-connected data transmission of the data stored in the device. The data is transmitted via a galvanically separated USB interface. At the same time, the device of the invention is charged by the power supply unit or is permanently supplied with current.

PC Software

The PC software serves to detect, store, process, visualize, evaluate, document, and archive patient-specific biophysical signals. This assists with the establishment of a diagnosis, therapeutic stabilization and therapeutic monitoring of sleep disturbances.

Device Software

The device software serves to detect, store, process and evaluate biophysical signals. This assists with the establishment of a diagnosis, therapeutic stabilization and therapeutic monitoring of sleep disturbances. The device software communicates with the PC software via a secure data transmission protocol.

Nonmedical Electrical Devices
reader for reading out the data stored on the CompactFlash® card;
online module for wireless data transmission (Bluetooth-USB adapter);
USB-TCP/IP converter;
PC system (external accessories).

The device of the invention generates information signals (e.g., rechargeable battery charge status), which are graphically visualized and stored by the display and/or the PC system. These information signals serve to check for the presence of signals to be recorded and to check the proper functioning of the device. This makes it possible to avoid faulty recordings, and an otherwise necessary repetition of the overnight measurement is avoided.

The automatic analyses (CWF, PTT, SpO2, pulse rate, PLM, snoring analysis, sleep stage analysis, arousal analysis, and cardiorespiratory analysis) can be carried out online in the device and/or offline from the signals stored in the PC and assist the evaluator in diagnosing sleep disturbances and in initiating and monitoring therapy.

The PC software is used for the visualization, evaluation, documentation and patient-specific archiving of long-term studies on the diagnostics of, for example, sleep disturbances, cardiovascular diseases, and diabetes. The system is configured for this, and the transmitted data is automatically analyzed offline. The software allows the input of comments by the user. Manual reclassification of the analytical results by the evaluator is possible.

After receiving directions from technical personnel and reading the patient instructions for use, the patient is able to apply the sensors and the device himself.

In the case of online analysis in the device, there is the possibility of directly responding to the analytical results, for example, by remote control of another device. It is possible, in the case of anesthesia, to control, for example, drug metering devices and/or ventilation machines, in the case of operators or pilots of a wide variety of transportation means (e.g., cars, trucks, trains, airplanes, etc.) to activate alarms, autopilot systems or the like on the basis of analytical results (e.g., lack of ability to concentrate, high level of tiredness, high sleep pressure), or, in the case of sleep medicine, to operate a therapeutic device (e.g., a CPAP machine) by remote control.

It is basically possible to use the device of the invention both in the prevention of various diseases (risk determination for secondary diseases) and in real-time scenarios in which a direct response is made to currently detected patterns.

The PC software is used for the visualization, evaluation, documentation and patient-specific archiving of long-term studies on the diagnostics of, for example, sleep disturbances, cardiovascular diseases, and diabetes. The system is configured for this, and the transmitted data is automatically analyzed offline. The software allows the input of comments by the user. Manual reclassification of the analytical results by the evaluator is possible.

After receiving directions from technical personnel and reading the patient instructions for use, the patient is able to apply the sensors and the device himself.

The device of the invention processes and stores all measured signals on the integrated memory unit, e.g., CompactFlash® card. The data are read out either via a USB cable or by reading out the CompactFlash® card with a reader. In clinical operation, the device of the invention can transmit the recorded data online, either wirelessly or by cable connection, to the software, where the data is additionally stored.

During online monitoring with the device of the invention, networks present in hospitals can be used. If data is lost, e.g., if the patient leaves the examination room, this data can be supplemented with the data stored on the CompactFlash® card. The device of the invention is powered by a replaceable battery pack, so that it is independent of the power network. Stored measured values are not lost during a battery change. The device can also be permanently powered and operated with the data transmission cable.

The device of the invention can also have an optional position sensor. The position sensor records whether and when the patient is prone, supine or lying on his side. The device can also have an optional effort sensor integrated in the housing. Integration reduces cleaning and increases the service life of the sensor.

A sensor test/impedance check can be initiated by a push button.

During a sensor test/impedance check, it can be determined by means of light-emitting diodes or an integrated display whether the electrodes and which electrodes are applied properly or poorly.

In addition, the device of the invention has a yellow light-emitting diode in the battery pack next to the battery symbol to indicate whether the rechargeable battery is presently charged. This information could also be indicated by a symbol on the integrated display. It is also possible to make an inquiry about the charge state via the software, since a capacity monitoring system is integrated in the rechargeable battery.

The stored data can be transmitted to the PC via the USB cable or via the converter box, in which a galvanic separation is integrated. The rechargeable battery can also be charged via the converter box with the power supply unit that is also provided. A battery pack can also be charged when it is not inserted in the device.

Function of the Software

The data transmitted during the measurement are stored and visualized. The data read in after the measurement are automatically analyzed according to time and value criteria. The software can carry out, for example, the following automatic analyses:

CWF analysis
snoring analysis
cardiorespiratory analysis
arousal analysis
sleep stage analysis On the basis of the analytical results and the displayed signals, the present results can be evaluated according to definable criteria.

Function of the Optional Sensors

Respiratory Flow/Snoring Eyeglasses

The respiratory flow/snoring eyeglasses in conjunction with the pressure sensor integrated in the device of the invention record the respiratory flow and snoring. Inspiration is recorded by the negative pressure that is generated, and expiration is recorded by the positive pressure that is generated. Snoring produces pressure fluctuations in the nostrils, and these fluctuations are likewise recorded. When the patient is breathing with his mouth closed, pressure measurement responds more sensitively to small flow limitations than thermal measurement. Pressure measurement is independent of the ambient temperature and, in addition, allows visual evaluation of the flow contour with respect to time. During mouth breathing, the signals can be attenuated. Alternatively, therefore, the respiratory flow oral sensor is used at the same time.

Pulse Oximetry Sensor

The pulse oximetry signals (the oxygen saturation of the blood, the pulse rate and a CWF signal) are measured by the pulse oximetry sensor.

The main components of the sensor are at least two light-emitting diodes and a receiver diode.

Several SpO2 values are determined for each pulse wave (split pulse wave algorithm).

The measured pulse rate variations correspond with sufficient accuracy to the heart rate variations that are triggered by a sleep apnea syndrome.

The variation of the pulse wave, especially the amplitude of the pulse wave, is determined by photoplethysmography.

The device of the invention computes a quality index for each oxygen saturation value that is determined. This quality index characterizes the quality or accuracy of the measured SpO2 value.

If the signal is disturbed by movements, the number of values is small. When the signals are undisturbed, the number of values is large. Accordingly, a disturbed test signal generates a low quality value, while an undisturbed test signal results in a high quality value. The quality signal assumes values between 0 and 100%. In the evaluation of SpO2 long-term measurements, the quality signal can be helpful, for it indicates artifacts that occurred during the measurement.

FIG. 1 shows a mobile unit with a pressure connection 1 for connection with a pressure measurement hose, electrode connections 2, an RIB 3, and a connection 4 for an abdomen sensor 35 (not shown). The drawing also shows LED's 5, which will be explained in greater detail below, a button 6, and a battery compartment latch 7. Also shown are a connection 8 for a battery-charge cable/data transfer cable and a rechargeable battery 9. Preferably, a second pressure connection 10 is provided. The functionality of the unit is further enhanced by a thorax sensor 11 and a connection 12 for a pulse oximeter sensor.

Figure 2:
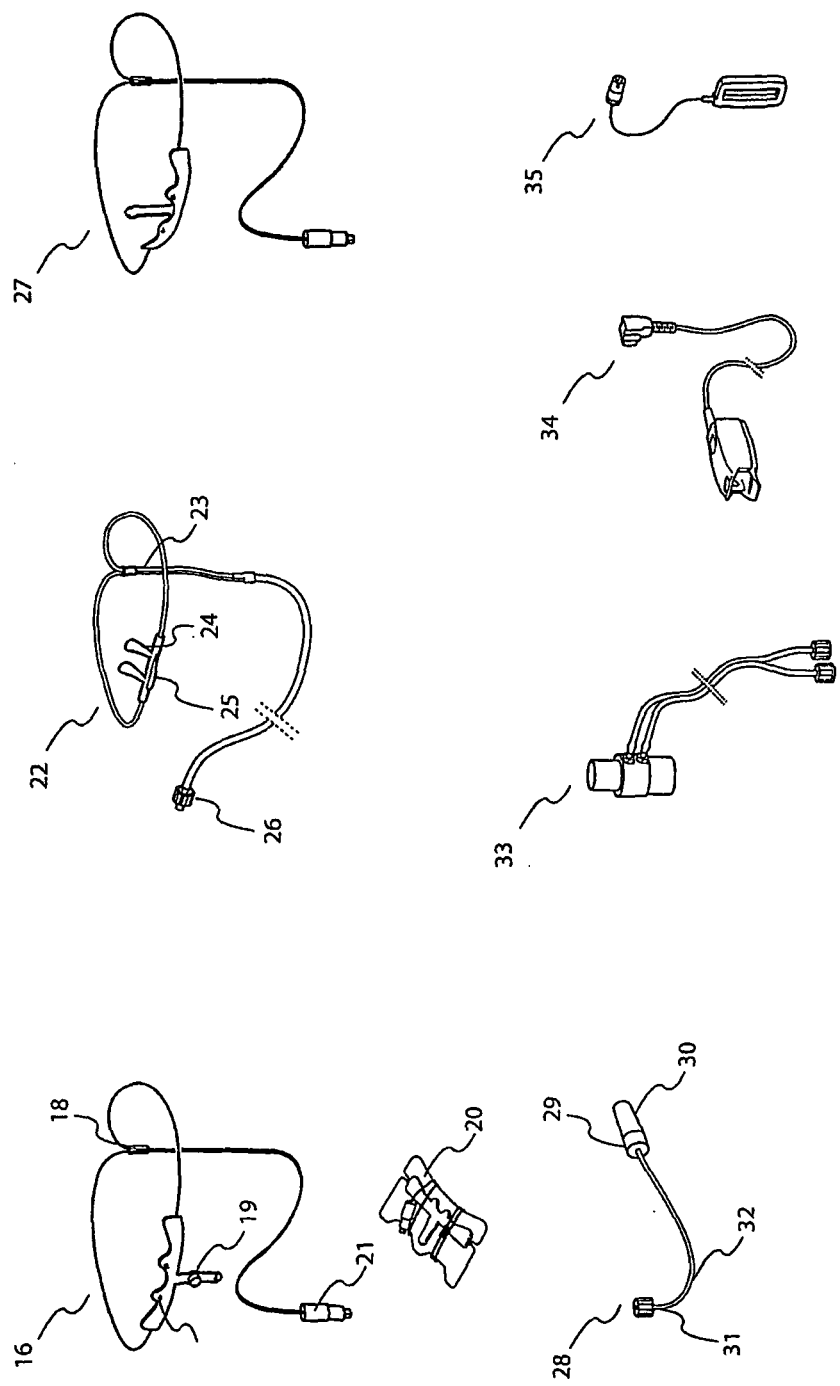
FIG. 2 shows adaptable sensors of the device.

An insert card with application sites is provided on the back of the mobile unit. FIG. 1 also shows a Z-electrode 14 and a connection 15. The connection 15 is used for connecting to a respiratory flow/snoring sensor 16 or a respiratory flow oral sensor 27, which are shown in FIG. 2. The connection 1 is provided for connection with respiratory flow/snoring eyeglasses 22 or a pressure measurement hose 28. The connections 1, 10 are used together for connecting with a pneumo-T-adapter 33.

In addition to the sensors for connection to the mobile unit that have already been mentioned, FIG. 2 shows sensor beads 17, a sleeve 18, a microphone 19, a mounting plate 20, and a sensor plug 21. The drawings also show a sleeve 23, canulas 24, a clip 25, and a connection 26 for the respiratory flow/snoring eyeglasses 22.

The pressure measurement hose 28 comprises a connecting piece 29, a connecting hose 30, a plastic hose 32, and a thread 31 for a CPAP connection. Other sensors shown in the drawings are a pulse oximetry sensor 34 and an abdomen sensor 35.

Figure 3:
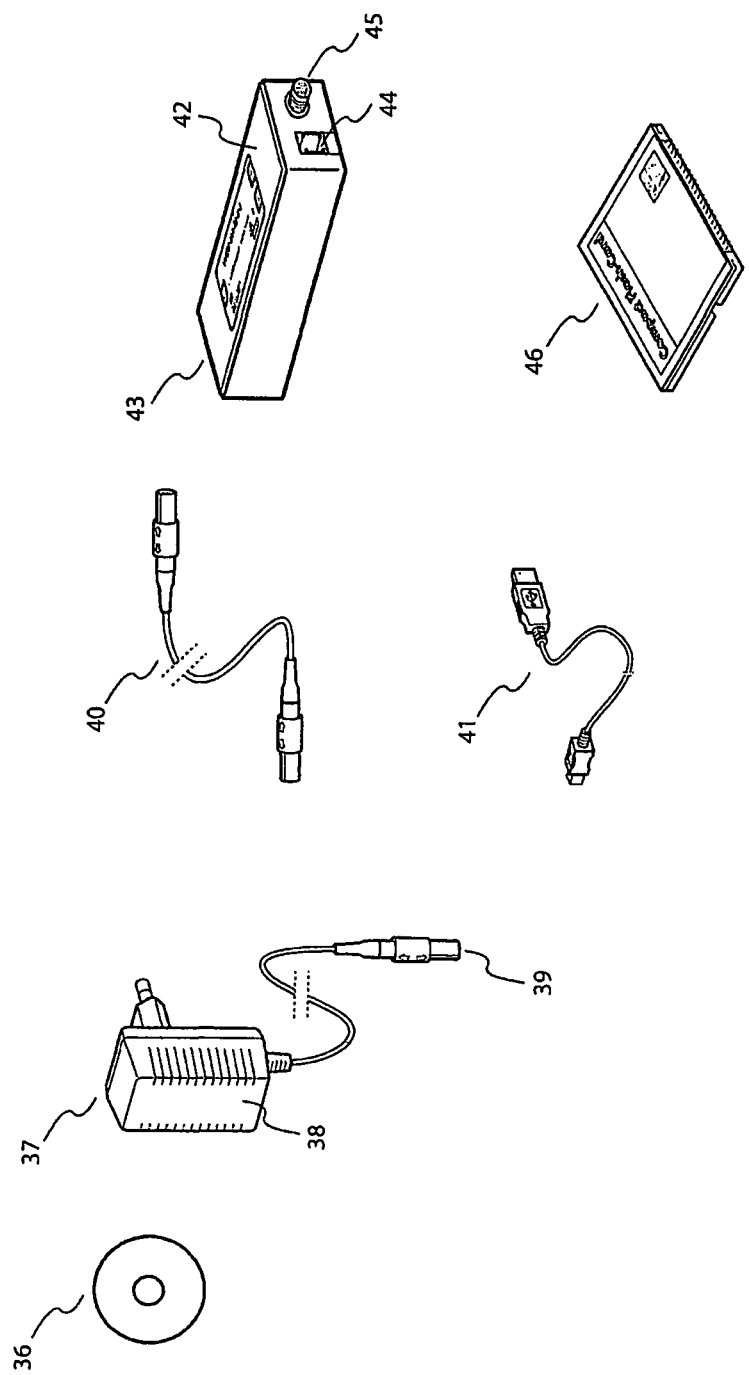
FIG. 3 shows peripherals of the device.

FIG. 3 shows components for the data transfer: The mobile unit is typically connected to an evaluation unit, which can be realized as a personal computer. In this regard, the evaluation unit comprises a CD-ROM drive with CD 36, a charger 37 with a power supply unit 38 and plug 39, a charge/data transfer cable 40, and a USB cable 41. A converter box 42 is equipped with a jack 43 for the charge/data transfer cable 40, a USB jack 44, and a charger jack 45. Data transmission from the mobile unit to the evaluation unit can also be effected directly by removing the memory card 46 from the mobile unit and inserting it into the evaluation unit.

FIG. 4 shows a device belt 47 and an abdominal belt 48 for assisting mobile use. The belts are used to fasten the device of the invention on a user. The belt is closed with a buckle. The belt can be adjusted to the girth of the body by adjusting the hook tapes. The belt consists of an elastic loop tape that is nonirritating to the skin.

Figure 5:
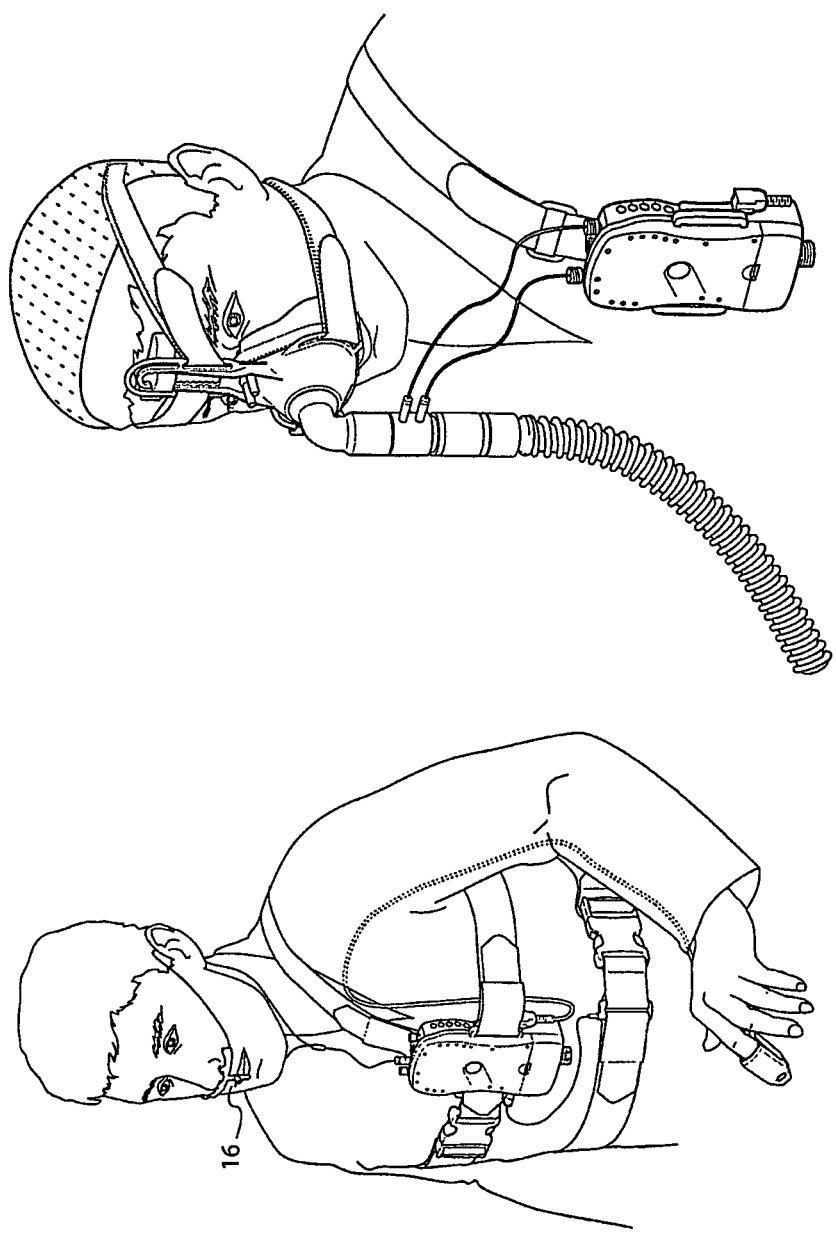
FIG. 5 shows the use of the device with adapted sensors.

The left side of FIG. 5 shows the use of the device of the invention with a respiratory flow/snoring sensor 16, and the right side shows its use for pressure measurement in a ventilator mask. The device is fastened on the user and is connected to a pulse oximetry sensor and a respiratory flow/snoring sensor (left) or is connected to a ventilator hose with a pneumo-T-adapter (right).

Figure 6:
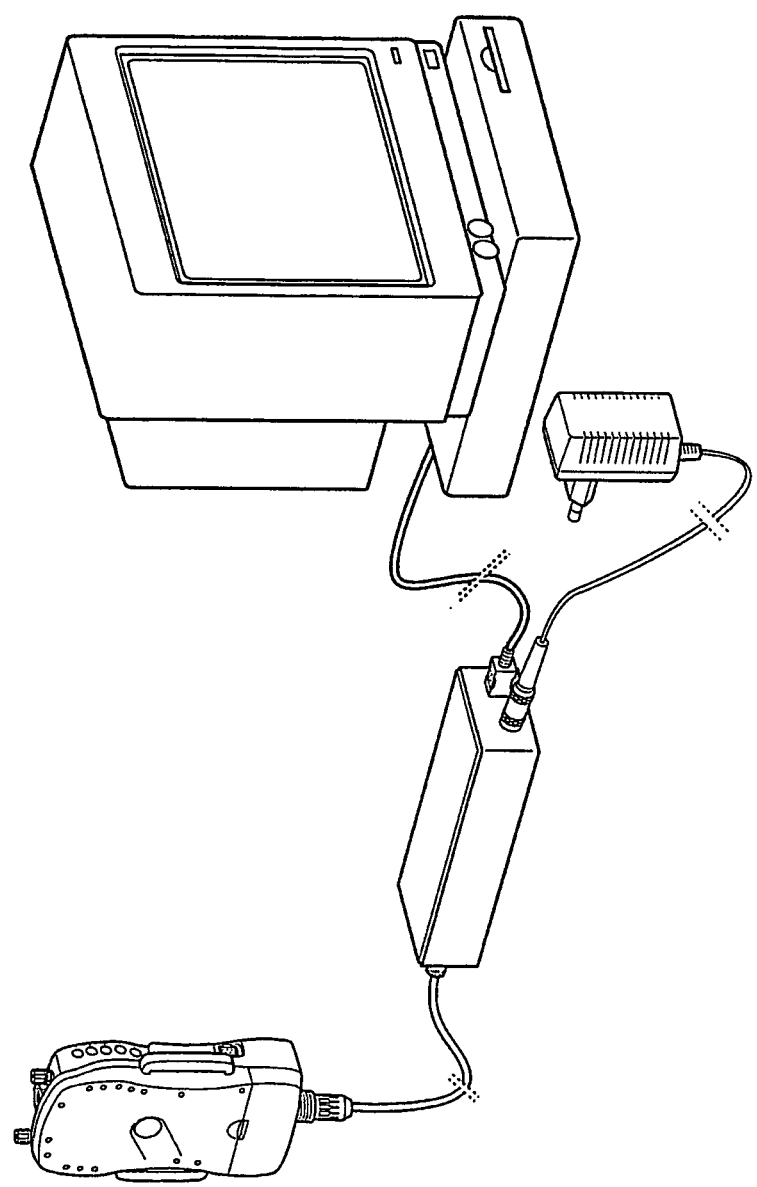
FIG. 6 shows a device with a connected computer and display device.

FIG. 6 shows a device connected to an evaluation unit, which is realized here as a personal computer. Data is transmitted to a PC via a medically acceptable power supply unit with an all-purpose cable for charging the rechargeable battery and for transmitting the stored data via a galvanically separated USB interface of the converter box. The converter box is used for cable-connected data transmission of the data stored in the device. The data is transmitted galvanically separately via a USB interface. At the same time, the device of the invention is charged via the power supply unit or permanently supplied with current. The PC software runs on the PC. The PC software serves to detect, store, process, visualize, evaluate, document, and archive patient-specific biophysical signals. This assists with the establishment of a diagnosis, therapeutic stabilization and therapeutic monitoring of sleep disturbances.

The pulse oximetry sensor 34 measures the pulse oximetry signals (the oxygen saturation of the blood and the pulse rate of the patient). The main components of the sensor are at least two light-emitting diodes and a receiver diode. For example, several SpO2 values are determined for each pulse wave (split pulse wave algorithm).

The measured pulse rate variations correspond with sufficient accuracy to the heart rate variations that are triggered by a sleep apnea syndrome.

Optionally, sensors are used, which, alternatively and/or additionally, make it possible to determine the concentration of hemoglobin (cHb), oxyhemoglobin (HbO2), deoxyhemoglobin (HbDe), carboxyhemoglobin (HbCO), methemoglobin (MetHb), sulfinethemoglobin (HbSulf), bilirubin, and glucose. To this end, the sensors have at least one light source, which alternatively and/or supplementally emits wavelengths selected from the following group of wavelength ranges: 150 nm±15%, 400 nm±15%, 460 nm±15%, 480 nm±15%, 520 nm±15%, 550 nm±15%, 560 nm±15%, 606 nm±15%, 617 nm±15%, 620 nm±15%, 630 nm±15%, 650 nm±15%, 660 nm±15%, 705 nm±15%, 710 nm±15%, 720 nm±15%, 805 nm±15%, 810 nm±15%, 880 nm±15%, 890±15%, 905 nm±15%, 910 nm±15%, 950 nm±15%, 980 nm±15%, 980 nm±15%, 1000 nm±15%, 1030 nm±15%, 1050 nm±15%, 1100 nm±15%, 1200 nm±15%, 1310 nm±15%, 1380 nm±15%, 1450 nm±15%, 1600 nm±15%, 1650 nm±15%, 1670 nm±15%, 1730 nm±15%, 1800 nm±15%, 2100 nm±15%, 2250 nm±15%, 2500 nm±15%, 2800 nm±15%.

The device of the invention computes a quality index for each oxygen saturation value that is determined. This quality index characterizes the quality or accuracy of the measured SpO2 value. If the signal is disturbed by movements, the number of values is small. When the signals are undisturbed, the number of values is large. Accordingly, a disturbed test signal generates a low quality value, while an undisturbed test signal results in a high quality value. The quality signal assumes values between 0 and 100%. In the evaluation of SpO2 long-term measurements, the quality signal can be helpful, for it indicates artifacts that occurred during the measurement.

Figure 7:
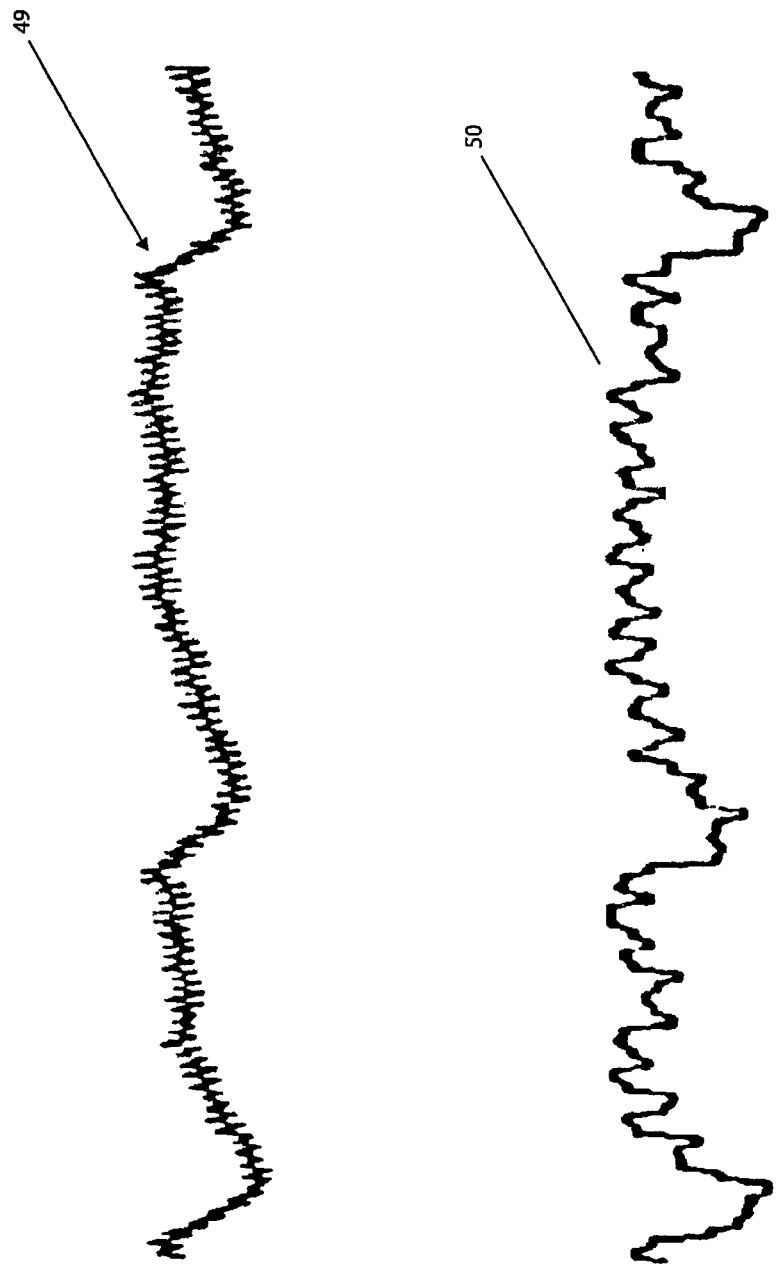
FIG. 7 shows a diagram of a sensor recording with a raw sensor signal and an extracted signal (CWF signal).

FIG. 7 shows the measured signal 49 as a raw plethysmogram. The plethysmogram 49 is subject to fluctuations. A CWF signal 50 is extracted from the plethysmogram 49. The CWF signal 50 contains information about the fluctuations of the plethysmogram. For example, the fluctuation can represent the pulse wave amplitude. It is also possible to represent the integral of the plethysmogram as a CWF.

Figure 8:
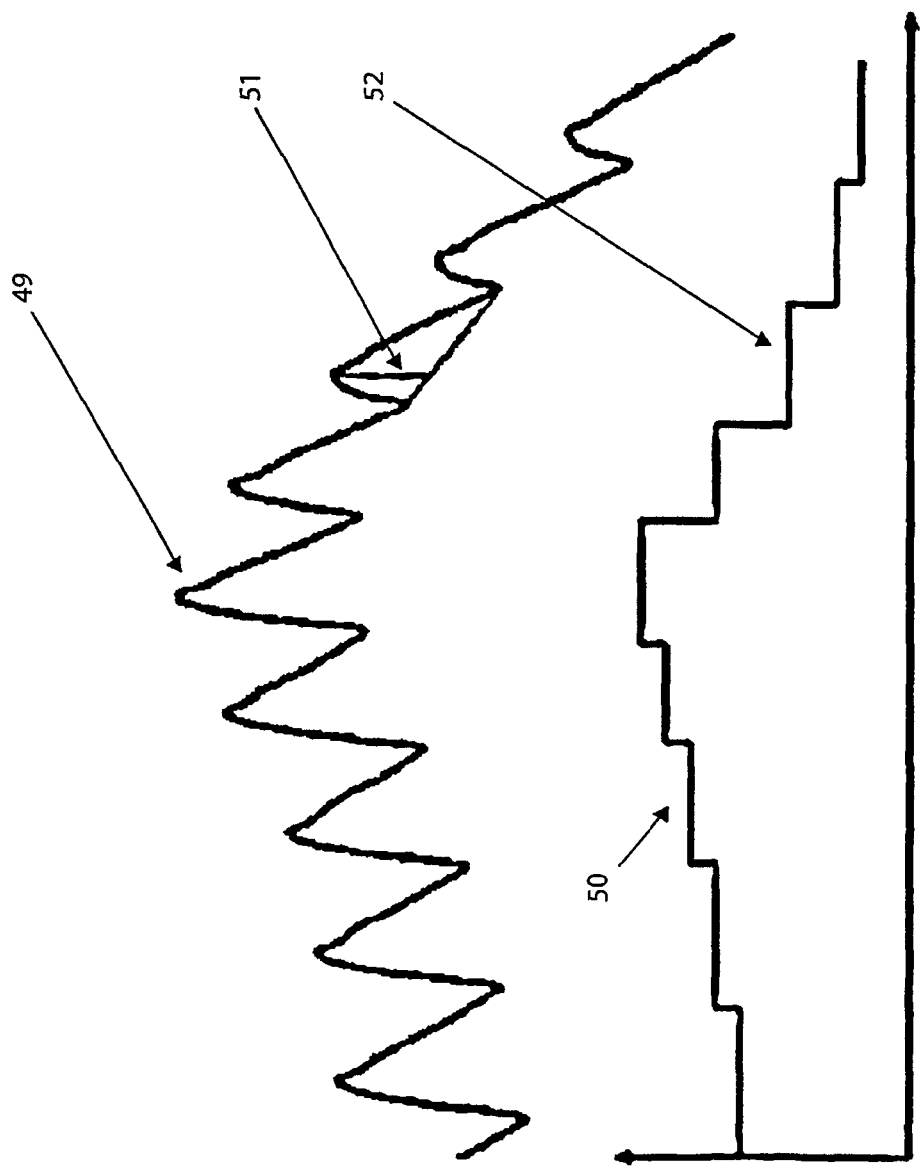
FIG. 8 shows a plethysmogram and an extracted signal (CWF signal) for representing the amplitude levels.

FIG. 8 shows a possible embodiment of the CWF signal. Here the amplitudes 51 of the plethysmogram 49 were used to determine the CWF signal. In this case, the CWF 50 represents the amplitude level of the plethysmogram 49.

However, it is also possible to use the PTT or other signals that are subject to fluctuations to determine a CWF.

In accordance with the invention, different signals can be combined to detect relevant fluctuations of the pulse wave and use them for the evaluation.

Thorax Sensor and Abdomen Sensor

Thorax and abdomen sensors are used to detect thoracic and abdominal respiratory movements.

In this regard, respiratory movements cause variable tensile stresses on the measuring pickups in the fastening belts. The measuring pickups use the piezoelectric effect to convert the movements to electrical signals.

The abdominal sensor, together with the abdominal belts, detects the abdominal respiratory movements. The sensor is made of a plastic that is nonirritating to the skin.

Electrophysiological Signals

The electrophysiological signals are measured by electrodes. Gold cup electrodes or adhesive electrodes can be used for this purpose.

electroencephalogram (EEG)
electrooculogram (EOG)
electromyogram (EMG)
electrocardiogram Respiratory Flow/Snoring Sensor Nasal and oral respiratory flow and snoring sounds are detected with the respiratory flow/snoring sensor. The sensor beads consist of thermistors. They detect the respiratory flow by the temperature of the exhaled and inhaled air. The microphone records the snoring sounds of the patient.

Respiratory Flow Oral Sensor 27

Oral respiratory flow is detected with the respiratory flow oral sensor during diagnosis with the respiratory flow/snoring eyeglasses, therapeutic stabilization, or therapeutic monitoring. The sensor beads consist of thermistors. They detect the respiratory flow by the temperature of the exhaled and inhaled air. The respiratory flow oral sensor 27 is used during diagnosis together with the respiratory flow/snoring eyeglasses or during therapeutic stabilization or therapeutic monitoring for detecting mouth breathing together with the pneumo-T-adapter 28.

Pneumo-T-Adapter 28

The pneumo-T-adapter is used together with a nasal mask for therapeutic monitoring. It is used for recording the respiratory flow and the snoring of the patient during therapy and for measuring the therapeutic pressure applied in the mask. Inspiratory and expiratory pressure fluctuations are conveyed from the mask to the device via the pressure measurement hoses. The exhalation of air generates a slight positive pressure, and the inhalation of air a slight negative pressure. The breaths taken by the patient can be derived from the pressure differences. Snoring sounds are measured by rapid pressure changes. The therapeutic pressure is derived from the static component of the pressure signal. The pneumo-T-adapter 28 is used together with xPAP machines during therapeutic stabilization and therapeutic monitoring. The pneumo-T-adapter can be used together with the respiratory flow oral sensor 27 to detect mouth breathing and mouth leakage. The pneumo-T-adapter has a standard tapered socket (ISO 22) for connection to therapy masks.

EXG Electrodes

The quantity detected with the electrodes is potential difference. A potential difference between two points of the body is being measured. Since the measurement on the skin surface is made noninvasively, the measurable potential differences are small. They are on the order of μV in the case of EEG's, EOG's, and EMG's and on the order of mV in the case of EKG's.

Bluetooth-USB Adapter

With the Bluetooth-USB adapter, data can be wirelessly received or transmitted online by the device of the invention, the device can be configured, and application monitoring can be carried out.

Network USB Server

The device of the invention can be operated over a network with the USB server. The USB server in conjunction with the Bluetooth-USB adapter enables the device of the invention to receive data wirelessly. In addition, the device can be configured, and application monitoring can be carried out. The device of the invention can also be cable-connected via the converter box.

CompactFlash® Card Reader

Data stored on the CompactFlash® card can be read out by the device of the invention with the CompactFlash® card reader. The device of the invention can also be configured via the CompactFlash® card reader and/or several CompactFlash® cards with different configurations can be installed.

Optional Modules

Supplementary PC software allows the therapeutic monitoring data to be read out and displayed, the remote control of all cited therapeutic apparatus via the software, and the PC-assisted evaluation of titration data from a ventilator titration instrument.

Combination with Therapeutic Systems

The device of the invention can be combined as a monitoring system with current CPAP, bilevel and APAP titration home ventilator therapeutic systems. The system can be connected quickly and easily by the pneumo-T-adapter, which is inserted between the hose and the mask.

Peripheral Devices

USB port: supported by Windows
connections: at least three free USB interfaces for connecting a card reader, a USB connecting cable to the data logger, and a Bluetooth®-USB adapter
graphics card: supported by Microsoft Windows, minimum resolution 1024×768, 16 bit color depth
monitor: 17" or larger CRT monitor or 15" or larger TFT monitor
mouse: Windows-compatible mouse
printer: supported by Microsoft Windows
network: network card 10/100 Mbit (only if the network-USB server is used)

Software

The software is used for analysis and offers alternative evaluation proposals. The evaluation of the automatically prepared analytical results is the responsibility of the physician. With each new programming of the device of the invention, the clock time in the basic device is synchronized with the system clock time of the PC. If data transmission to the PC is interrupted, the measurement data continues to be stored in the device. In the software, the signals are represented as the zero line. All data can be read out.

As with the EMG's, bipolar derivations are also used for the EKG. The polysomnographic derivation of the device of the invention is based on the Einthoven derivation. The reference electrode in the device of the invention is the ground electrode on any part of the body.

The device of the invention can be attached to the patient by means of belts, which can be guided in eyes (a, b, c) located on the sides of the device. The belts can be adjusted to the girth of the patient by hook tapes. The belt consists of an elastic loop tape that is nonirritating to the skin.

Carrying Out a Sensor Test

To check that all of the sensors are properly connected, a test can be performed after the sensors and devices have been attached. This is done by pressing the button 6.

| Operation | Device |
|---|---|
| Sensor test is running | During the sensor test, the LED of the sensor now being tested blinks fast (4 × per second). |
| Sensor test OK | The LED of the corresponding signal stops blinking after completion of the impedance test: impedance of the electrode < 5 kΩ OK, or sensor signal present. |
| Sensor testing means | The LED of the corresponding signal blinks slowly after completion of the impedance test: impedance of the electrode < 10 kΩ not optimal but of acceptable quality. Green LED's blink slowly at 0.5 Hz. |
| Sensor test not OK | The LED of the corresponding signal blinks fast after completion of the impedance test: impedance of the electrode > 10 kΩ or no sensor signal (check electrode and sensor, unacceptable signal quality). Green LED's blink fast at 1 Hz. |

After successful application of all configured electrodes/sensors, no LED is still lighted on the device of the invention. There is then no longer any change in state of the LED's on the device of the invention when, in the next step, the sensor test is ended by closing the impedance window in the software.

During the sensor test, all channels, i.e., including effort sensors and pulse oximetry sensors, as well as thermistors and eyeglasses, are tested for the presence of a signal. If the LED is off, this means: "The sensor is connected and is transmitting a (physiological) signal".

An impedance test always runs once through all configured channels and then shows its result until the window is closed or a new test is started.

| | |
|---|---|
| Product Class according to 93/42/EU | IIa |
| Dimensions (W × H × D) | 80 × 150 × 34 |
| Weight (device without sensors) | About 300 g |
| Temperature range: | |
| Operation | +5° C. to +40° C. |
| Storage | −10° C. to +60° C. |
| Power supply voltage, basic device | 3.7 V dc |
| Power supply voltage, rechargeable battery | 7.5 V dc |
| Mean power consumption | About 340 mW |
| Rechargeable battery operating time: | |
| wireless online | About 10 hours |
| ambulatory | About 20 hours |
| Max. recording time for a measurement | 12 hours |
| Electrical connection, power supply unit | Input: 100-240 V 50-60 Hz, 400 mA Output: 7.5 V dc |
| Classification according to EN 60601-1 | |
| type of protection against electric shock | Protective class II |
| degree of protection against electric shock | Type BF |

-continued

| | |
|---|---|
| Electromagnetic compatibility (EMC) according to EN 60601-1-2 | (The test parameters and limiting values can be requested from the manufacturer if necessary.) |
| noise suppression | EN 55011 |
| immunity to noise | EN 61000-4, Parts 2 to 6, Part 11 |
| Type of protection against water penetration | IPX-0 |
| Relative humidity during operation and storage | 25 to 95%, noncondensing |
| Air pressure during operation and storage | 700 to 1060 hPa |
| Data recording medium | CompactFlash ® card, max. 512 MB |
| Data transmission online | wireless by radio signal at 2.4 GHz USB 1.1 or higher (galvanically separated) |
| Readout of the stored data | USB 1.1 or higher Removal of the CompactFlash ® card, reading in by CompactFlash ® card reader |

Radio Module

| | |
|---|---|
| Carrier frequency | 2400 MHz to 2483.5 MHz |
| Transmit power | 0 dBm average (Class 2) |
| Hopping frequency | f = 2402 + k MHz, k = 0, . . . 78 |
| Guard band | 2 MHz < f < 3.5 MHz in the USA, Japan, Europe |

Rechargeable Battery

| | |
|---|---|
| Type of rechargeable battery | Li ion |
| Voltage | 3.7 V |
| Capacity | 2.15 Ah |
| Overvoltage | 4.35 V |
| Max. charging current | 1 A |
| Discharge current, normal | <1 A |
| Temperature range | −20 to +85° C. |
| Charging cycles | 500 |
| Charging time with the device shut off | About 3 hours at 25° C. and empty battery |

Position Sensor

| | |
|---|---|
| Position sensor | sensor integrated in the device |
| Range of values | right side, left side, prone, supine, standing |
| Accuracy, position | about 45° ± 15° |

CPAP/BiPAP/SmartPAP

| | |
|---|---|
| pressure measurement range | 0 to 40 hPa |
| Accuracy | ±0.6 hPa |

Pulse Oximetry Clip Sensor

| | |
|---|---|
| SpO2 measurement range | 50 to 100% |
| SpO2 accuracy | 70% < SpO2 < 100% better than 2% SpO2 accuracy |

Pulse Rate

| | |
|---|---|
| Measurement range | 30 to 250 bpm |
| Pulse accuracy | ±1 bpm up to 2% from the displayed value |
| Signal quality | >90% |

Respiratory Flow

| | |
|---|---|
| Respiratory flow/ snoring sensor | 3 thermistors as a composite signal, no measuring function at ambient temperatures of 33-38° C. |
| Respiratory flow/ snoring eyeglasses | inspiratory/expiratory pressure fluctuations |
| Respiratory flow oral sensor | one thermistor, no measuring function at ambient temperatures of 33-38° C. |

Electrophysiological Signals

| Channel | EKG | EEG | EMG | EOG |
|---|---|---|---|---|
| Dynamic range (physical range of values) | ±5 mV | ±500 µV | ±250 µV | ±500 µV |
| Resolution | 12 bit | 12 bit | 12 bit | 12 bit |
| Lower frequency limit | 0.16 Hz | 0.5 Hz | 2.7 Hz | 0.5 Hz |
| Upper frequency limit | 100 Hz | 100 Hz | 500 Hz | 100 Hz |
| Accuracy | ±3% | ±3% | ±3% | ±3% |
| Adjustable are | EMG, EOG, EEG, EKG | | | |
| Specification | as EMG, EOG, EEG, EKG | | | |
| Input impedance | About 40 MΩ | | | |

Technical Data of Nonmedical Components

Flow Differential Pressure

| | |
|---|---|
| Pneumo-T-adapter | tapered socket according to standard ISO 22 |
| Sensor | differential pressure; inspiratory/expiratory pressure fluctuations |

Effort Sensors (Thorax, Abdomen)

| | |
|---|---|
| Thorax sensor | sensor integrated in the device |
| Method | piezoelectric measurement |

Snoring

| | |
|---|---|
| Respiratory flow/ snoring sensor | integrated microphone |
| Respiratory flow/ snoring eyeglasses | pressure sensor |
| Pneumo-T-adapter | pressure sensor |
| Method | logarithmic mean value of the sound pressure signal (microphone) or of the pressure fluctuations (pressure sensor) |

Electrodes

| Touch-safe plug connector, according to DIN 42802 | 1.5 mm |
|---|---|

The invention claimed is:

1. A device for determining a reference value of biophysical data of an individual for determining an individual risk, said device comprising: at least one sensor for noninvasive measurement of at least three signals, which are CWF (continuous wave fluctuation), SpO2, heart rate; and an evaluation unit connected to the sensor, where the evaluation unit has at least one analyzer adapted to determine signal ranges that are definable by signal analysis, wherein the evaluation unit includes a comparator adapted to coordinate the signal ranges by taking additional parameters into account, and to produce a result that is output as an index value, wherein the sensor is a pulse oximeter adapted to record a plethysmogram and SpO2, wherein the evaluation unit extracts CWP's (continuous wave parameters) from the plethysmogram, the evaluation unit extracting the following as CWP's: pulse wave amplitude, a ratio of different integrals over different intervals of the plethysmogram, a quantity related to PTT (pulse transit time), the evaluation unit being adapted to compute a CWF (continuous wave fluctuation) signal from the CWP's as a function of time, wherein the CWF signal contains information about fluctuations of the plethysmogram or the CWP's derived from the plethysmogram, the signals being analyzed by pattern recognition and compared with stored values, the comparison providing a result that yields a patient-specific risk index that is suitable for predicting a risk of cardiovascular disease.

2. A device in accordance with claim 1, wherein the additional parameters include existing biophysical data of the individual and/or static data sets.

3. A device in accordance with claim 2, wherein the static data sets are compiled from groups of individuals, and include medication, age, sex, and diagnostic data.

4. A device in accordance with claim 1, wherein the comparator is adapted to be connected to peripheral devices.

5. A device in accordance with claim 1, wherein the evaluation unit is adapted for determining the CWF both from the at least one detected test signal and the CWP.

6. A method for determining an individual risk for an individual, comprising the following steps:
determining measurement data of at least three heart-specific and/or circulation-specific and/or respiration-specific parameters of the user, selected from the group comprising: continuous wave fluctuation (CWF), SpO2, SaO2, pulse rate, heart rate, and blood pressure by at least one noninvasive sensor device;
determining the measurement data over a period of at least one minute;
determining measurement data with a synchronized time recording;
bringing together time information and the measurement data;
analyzing the measurement data with the time information being taken into account;
carrying out the analysis as a pattern recognition, including, at least in intervals, detecting a course of the measurement with respect to time of at least one parameter can be and evaluating the course with respect to a typical individual pattern and/or a progressive pattern to identify user-specific individual patterns and/or patterns of development;
analyzing as to whether the identified user-specific individual patterns and/or patterns of development are comparable in a user-specific way with definable threshold values to identify threshold value deviations; and
analyzing as to whether the identified threshold value deviations of the user-specific individual patterns and/or patterns of development are quantified and/or can be qualified
wherein the measured data is determined using a pulse oximeter, wherein the sensor is a pulse oximeter adapted to record a plethysmogram and SpO2, wherein the evaluation unit extracts CWP's (continuous wave parameters) from the plethysmogram, the evaluation unit extracting the following as CWP's: pulse wave amplitude, a ratio of different integrals over different intervals of the plethysmogram, a quantity related to PTT (pulse transit time), the evaluation unit being adapted to compute a CWF (continuous wave fluctuation) signal from the CWP's as a function of time, wherein the signals are analyzed by pattern recognition and compared with stored values to provide a result that yields a patient-specific risk index that is suitable for predicting a risk of cardiovascular disease.

7. A method in accordance with claim 6, including determining at least one user-specific risk index value that is representative of the heart-specific and/or circulation-specific and/or respiration-specific parameter of the user from the quantification and/or qualification of the threshold value deviations.

8. A method for evaluating at least one test signal, comprising the steps of: detecting at least one test signal with at least one sensor; and computing a CWP (continuous wave parameter) from the at least one test signal, wherein the sensor is a pulse oximeter adapted to record a plethysmogram and SpO2, wherein the evaluation unit extracts CWP's (continuous wave parameters) from the plethysmogram, the evaluation unit extracting the following as CWP's: pulse wave amplitude, a ratio of different integrals over different intervals of the plethysmogram, a quantity related to PTT (pulse transit time), the evaluation unit being adapted to compute a CWF (continuous wave fluctuation) signal from the CWP's as a function of time, wherein the CWF signal contains information about fluctuations of the plethysmogram or the CWP's derived from the plethysmogram, the signals are analyzed by pattern recognition and compared with stored values to provide a result that yields a patient-specific risk index that is suitable for predicting a risk of cardiovascular disease.

9. A method in accordance claim 8, including computing the CWF from at least one test signal.

10. A method in accordance with claim 8, including computing the CWF from the at least one test signal and the CWP.

11. A method in accordance with claim 9, including evaluating the CWF for controlling a device.

12. A device for determining and analyzing biophysical data of an individual, which device comprises a basic module with a power supply, a memory unit, and at least one sensor device for noninvasive measurement of at least three test signals that represents cardiac activity and/or respiratory activity, which is selected from the following group: pulse rate, plethysmogram, oxygen saturation, respiratory signal, and heart signal; and an analyzer connected to the sensor device for extracting at least one CWP (continuous wave parameter) from the test signals, and a device adapted for determining at least one CWF (continuous wave fluctuation), wherein the CWF (continuous wave fluctuation) is determined from the CWP and/or the test signal, wherein the sensor is a pulse oximeter adapted to record a plethysmogram and SpO2, wherein the evaluation unit extracts CWP's (continuous wave parameters) from the plethysmogram, the evaluation unit extracting the following as CWP's: pulse wave amplitude, a ratio of different integrals over different intervals of the plethysmogram, a quantity related to PTT (pulse transit time), the evaluation unit being adapted to compute a CWF (continuous wave fluctuation) signal from the CWP's as a function of time, wherein the CWF signal contains information about fluctuations of the plethysmogram or the CWP's derived from the plethysmogram, wherein the signals are analyzed by pattern recognition and compared with stored values to provide a result that yields a patient-specific risk index that is suitable for predicting a risk of cardiovascular disease.

13. A device in accordance with claim 12, further comprising a classifier adapted to compare at least one CWF datum and/or quantities derived from the CWF datum with stored data for identifying physiological/pathophysiological events.

14. A device in accordance with claim 12, further comprising a classifier adapted to compare at least one CWF datum and/or quantities derived from the CWF datum with other test signals and/or CWP's for identifying physiological/pathophysiological events.

15. A device in accordance with claim 13, wherein at least some of the results of the analyzer and/or at least some of the results of the classifier are output basically immediately, acoustically, and/or graphically.

16. A device in accordance with claim 12, wherein the analyzer is adapted to evaluate at least two signals that are temporally related to identify physiological events.

17. A device in accordance with claim 12, further comprising supplementary modules adapted for measuring other signals.

18. A device in accordance with claim 12, further comprising at least one interface installed in the basic module, where the interface is adapted to permit data to be read out and/or other devices to be controlled.

19. A device in accordance with claim 12, further comprising supplementary sensor devices adapted for measuring other signals.

20. A device in accordance with claim 1, wherein the sensor device is selected from the group comprising: EKG, EMG, EOG, EEG, pulse oximetry, blood pressure, impedance measurement, ultrasound, Doppler, CO2, respiratory flow, snoring, mouth, thorax, abdomen, and position sensors.

21. A device in accordance with claim 1, further comprising a module adapted to determine other biophysical data.

22. A device in accordance with claim 1, further comprising a module adapted to determine other respiratory parameters.

23. A device in accordance with claim 1, further comprising a module adapted to determine other cardiological parameters.

24. A device in accordance with claim 1, further comprising a data input device adapted for inputting patient data.

25. A device in accordance with claim 1, further comprising a display device and/or an output device adopted to display and/or output analytical results.

26. A device in accordance with claim 1, further comprising a fastening assembly for fastening the device on a body of an individual.

27. A device for determining and analyzing biophysical data of an individual, comprising: at least one sensor device for the noninvasive measurement of at least three signals, including a plethysmogram and CWF (continuous wave fluctuation) signals derived from the plethysmogram, SpO2 and pulse rate; and an analyzer connected to the sensor device for analyzing transient and/or periodically recurring patterns of the measured signals, which analyzer has at least one module adapted for evaluation of information that is related to frequency or amplitude of the signals or parameters derived from the signals, wherein the sensor is a pulse oximeter adapted to record a plethysmogram and SpO2, wherein the evaluation unit extracts CWP's (continuous wave parameters) from the plethysmogram, the evaluation unit extracting the following as CWP's: pulse wave amplitude, a ratio of different integrals over different intervals of the plethysmogram, a quantity related to PTT (pulse transit time), the evaluation unit being adapted to compute a CWF (continuous wave fluctuation) signal from the CWP's as a function of time, wherein the CWF signal contains information about fluctuations of the plethysmogram or the CWP's derived from the plethysmogram, the signals are analyzed by pattern recognition and compared with stored values to provide a result that yields a patient-specific risk index that is suitable for predicting a risk of cardiovascular disease.

28. A method for determining and analyzing biophysical data of an individual, comprising the steps of: noninvasively measuring at least three signals using at least one sensor device, the two signals being selected from the group comprising a plethysmogram with CWF (continuous wave fluctuation) signals derived from the plethysmogram, SpO2 signals and pulse rate; determining transient and/or periodically recurring patterns of the measured signals with an analyzer connected to the sensor device; and further processing, based on results from the analyzer, information which is related to frequency and/or amplitude of the signals or parameters derived from the signals, wherein the sensor is a pulse oximeter adapted to record a plethysmogram and SpO2, wherein the evaluation unit extracts CWP's (continuous wave parameters) from the plethysmogram, the evaluation unit extracting the following as CWP's: pulse wave amplitude, a ratio of different integrals over different intervals of the plethysmogram, a quantity related to PTT (pulse transit time), the evaluation unit being adapted to compute a CWF (continuous wave fluctuation) signal from the CWP's as a function of time, wherein the CWF signal contains information about fluctuations of the plethysmogram or the CWP's derived from the plethysmogram, the signals are analyzed by pattern recognition and compared with stored values to provide a result that yields a patient-specific risk index that is suitable for predicting a risk of cardiovascular disease.

29. A device in accordance with claim 2, wherein the additional parameters of the existing biophysical data of the individual include medication, medical history, age, sex, diagnostic data.

30. A device in accordance with claim 4, wherein the peripheral devices are selected from the group consisting of computers, printers and display devices.

* * * * *